(12) United States Patent
Knight

(10) Patent No.: US 7,760,099 B2
(45) Date of Patent: Jul. 20, 2010

(54) RADIO FREQUENCY VERIFICATION SYSTEM AND DEVICE

(75) Inventor: Thomas F. Knight, Trabuco Canyon, CA (US)

(73) Assignee: Codan US Corporation, Santa Ana, CA (US)

( * ) Notice: Subject to any disclaimer, the term of this patent is extended or adjusted under 35 U.S.C. 154(b) by 640 days.

(21) Appl. No.: 11/556,596

(22) Filed: Nov. 3, 2006

(65) Prior Publication Data

US 2008/0106388 A1 May 8, 2008

(51) Int. Cl.
*G08B 13/00* (2006.01)
(52) U.S. Cl. ............... 340/572.8; 340/572.1; 340/10.1
(58) Field of Classification Search ............ 340/572.8, 340/572.1, 572, 10, 505
See application file for complete search history.

(56) References Cited

U.S. PATENT DOCUMENTS

| | | | |
|---|---|---|---|
| 5,448,846 A | 9/1995 | Peterson et al. | |
| 5,986,562 A | 11/1999 | Nikolich | |
| 6,469,627 B1 | 10/2002 | Forster et al. | |
| 6,980,111 B2 | 12/2005 | Nolte | |
| 7,042,357 B2 | 5/2006 | Girvin et al. | |
| 7,161,488 B2* | 1/2007 | Frasch | 340/572.1 |
| 7,262,699 B2* | 8/2007 | Marsilio et al. | 340/572.1 |
| 7,394,383 B2* | 7/2008 | Hager et al. | 340/572.8 |
| 7,456,745 B2* | 11/2008 | Marsilio et al. | 340/572.1 |
| 2001/0028308 A1* | 10/2001 | De La Huerga | 340/573.1 |
| 2004/0008123 A1* | 1/2004 | Carrender et al. | 340/825.49 |
| 2005/0009122 A1 | 1/2005 | Whelan et al. | |
| 2005/0017865 A1* | 1/2005 | Belden | 340/572.9 |
| 2005/0073419 A1 | 4/2005 | Gary, Jr. | |
| 2005/0091896 A1 | 5/2005 | Kotik et al. | |
| 2005/0151652 A1* | 7/2005 | Frasch | 340/573.1 |
| 2005/0174241 A1 | 8/2005 | Olsen | |
| 2005/0184874 A1 | 8/2005 | Mosher, Jr. | |
| 2005/0237205 A1* | 10/2005 | Gorst | 340/572.9 |
| 2005/0258937 A1 | 11/2005 | Neuwirth | |
| 2006/0086808 A1* | 4/2006 | Appalucci et al. | 235/492 |
| 2006/0109118 A1 | 5/2006 | Pelo et al. | |
| 2006/0145856 A1 | 7/2006 | Tethrake et al. | |
| 2006/0145866 A1* | 7/2006 | Marsilio et al. | 340/572.8 |
| 2006/0145871 A1 | 7/2006 | Donati et al. | |
| 2006/0152367 A1 | 7/2006 | Narayanaswamy | |
| 2006/0152368 A1 | 7/2006 | Turner et al. | |
| 2006/0152371 A1* | 7/2006 | Marsilio et al. | 340/572.9 |
| 2007/0188329 A1* | 8/2007 | Garcia et al. | 340/572.8 |
| 2007/0262876 A1* | 11/2007 | Marsilio et al. | 340/572.8 |
| 2008/0048868 A1* | 2/2008 | Chua et al. | 340/572.8 |
| 2008/0111696 A1* | 5/2008 | Chisholm | 340/572.8 |
| 2008/0149584 A1* | 6/2008 | Martinelli | 215/201 |
| 2008/0284567 A1* | 11/2008 | Portier et al. | 340/10.1 |
| 2009/0043253 A1* | 2/2009 | Podaima | 604/67 |

* cited by examiner

*Primary Examiner*—Travis R Hunnings
(74) *Attorney, Agent, or Firm*—Sheppard Mullin Richter & Hampton LLP

(57) ABSTRACT

The present invention provides a tracking device for communicating information regarding an object, the tracking device comprising a housing including a disk having a central axis and an outer circumference, and a plurality of arms attached to the outer circumference of the disk forming a cavity. The tracking device further comprises a transponder disposed within the cavity and configured to transmit an electromagnetic signal in response to an electromagnetic wave, the transponder including an integrated circuit having a memory and an antenna electrically coupled to the integrated circuit.

5 Claims, 4 Drawing Sheets

RADIO FREQUENCY VERIFICATION SYSTEM AND DEVICE

FIELD OF THE INVENTION

The invention broadly relates to a system and device for verifying identity and/or procedures prior to undertaking a particular course of action and more particularly to a radio frequency verification system and device for ensuring patient safety within a medical environment.

BACKGROUND OF THE INVENTION

As health care grows increasingly complex with the growing number of available drugs, procedures, and technology, the potential for mistaken identification, mix-ups, or otherwise errors in the medical environment is increasing exponentially. Conventional methods of error prevention include the use of written labels born by medicament containers. Such methods suffer from a number of drawbacks. For example, a written label is not useful if its associated container becomes lost. In addition, there is a limited amount of information that can be practically fit on a label. Moreover, bar codes and similar coded labels can deteriorate over time or become unreadable due to smudging or tearing.

SUMMARY OF THE INVENTION

The present invention provides a tracking device for communicating information regarding an object, the tracking device comprising a housing including a disk having a central axis and an outer circumference, and a plurality of arms attached to the outer circumference of the disk forming a cavity. The tracking device further comprises a transponder disposed within the cavity and configured to transmit an electromagnetic signal in response to an electromagnetic wave, the transponder including an integrated circuit having a memory and an antenna electrically coupled to the integrated circuit.

According to the invention, the tracking device includes a transponder disposed within the cavity and configured to transmits an electromagnetic signal in response to an incident electromagnetic wave. The transponder comprising includes an integrated circuit having a memory and an antenna electrically coupled to the integrated circuit. The transponder generate power from the incident electromagnetic wave to power the integrated circuit.

In one embodiment, the tracking device has arms that are flexible and extend from the disk at an acute angle with respect to the central axis to form the cavity. The disk may include a tapered edge to provide leverage in removal of the tracking device from an object. The tracking device may include a ridge disposed within the cavity for preventing damage to the transponder. According to some embodiments, the tracking device has a series of raised portions on the disk for increased traction with respect to a user's finger.

In another embodiment, the tracking device has arms with a flared end that is oriented in a direction radial to the central axis of the disk, and the tracking device has a groove disposed within the cavity and is configured to receive a disk shaped mating surface. The tracking device may further comprise a well on the disk and within the cavity that is dimensioned to receive a portion of the transponder. According to further embodiments, the tracking device may include a second well within the well dimensioned to receive another portion off the transponder.

In a further embodiment, the tracking device transmits a signal that contains information for tracking the object, and generates a signal that contains medical information. By way of example, the medical information may comprise patient and drug identification.

In another embodiment, a radio frequency safety system for a drug container is provided. The system includes a housing attached to the drug container. The housing has a cavity and a radio frequency identification tag (RFID tag). The RFID tag is disposed within the cavity, and transmits a radio frequency signal in response to an incoming radio frequency signal. The transmitted radio frequency signal contains tracking information and drug identification information. The radio frequency safety system may include a disk having an outer circumference and a plurality of arms. The arms are attached to the outer circumference of the disk and form a cavity.

According to the invention, the radio frequency safety system includes a housing that is snap-fit onto the distal end of a plunger of a syringe. In some embodiments, the a housing includes a disk having a central axis, an outer circumference and a plurality of arms that are flexibly attached to the outer circumference of the disk. The arms descend from the disk forming a cavity and the tracking device is disposed between the disk and a mating surface of a medical container. In accordance with the principles of the invention, the housing is attached to an object such as a syringe.

In yet another embodiment, a transponder is disposed within the cavity of the housing and is configured to transmit an electromagnetic signal in response to an electromagnetic wave. The transponder includes an integrated circuit having a memory and an antenna electrically coupled to the integrated circuit.

DETAILED DESCRIPTION

Figure 1:
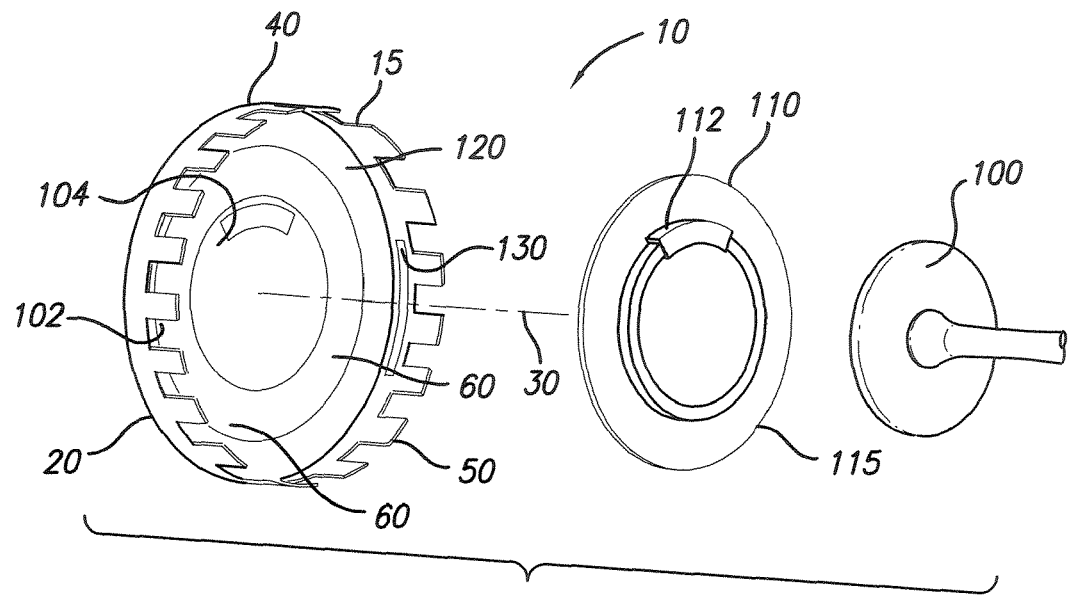
FIG. 1 is an illustration of a preferred verification system and device, in accordance with the principles of the present invention.
Figure 2:
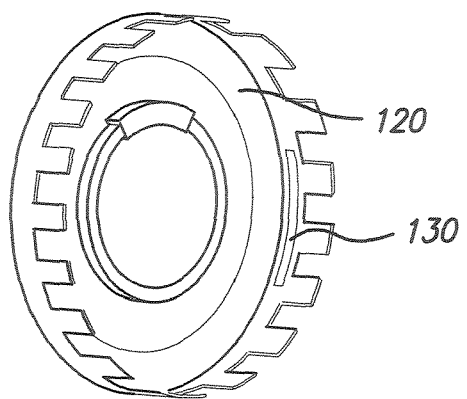
FIG. 2 is an illustration of a preferred verification system and device depicting a housing containing a transponder.
Figure 3:
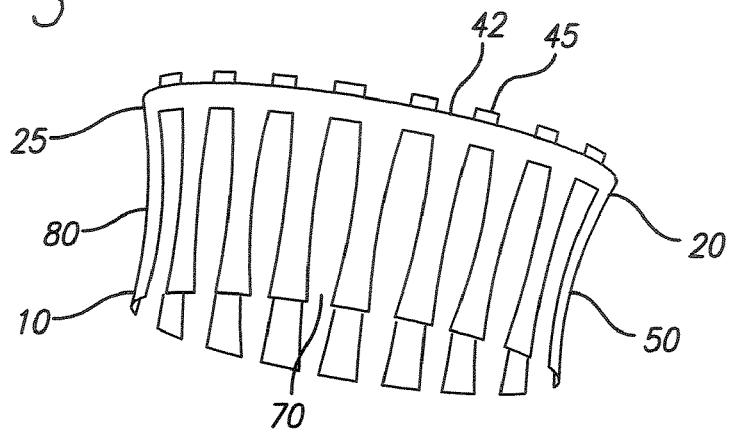
FIG. 3 is a side view of a preferred verification system and device.

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

FIGS. 1-6 illustrate a preferred radio frequency verification device 10 in accordance with the present invention. In particular, the device 10 includes a housing 15 that may be composed of molded thermoplastic or a thermo set polymer material. In the illustrated embodiment, the housing 15 comprises a disk 20 with a tapered edge 25, a central axis 30 and an outer circumference 40. A top side 42 of the disk 20 may include raised portions 45 for improved traction with respect to a user's finger while handling the device 10. The tapered edge 25 of the disk 20 provides leverage in the removal of the device from an object, which may comprise a medical container. By way of example, the medical container may comprise a syringe having a plunger, and the device 10 may be attached to a portion of the syringe such as the distal end of the plunger. As will be appreciated by those of ordinary skill, the device 10 may be attached to other types of objects or medical containers without departing from the scope of the invention.

With continued reference to FIGS. 1-6, the device 10 further comprises a plurality of arms 50 attached to the outer circumference 40 and on an underside 60 of the disk 20. The arms 50 have two segments 80, 90 which include an upper segment 80 that extends from the disk 20 at an acute angle with a normal 30 of the disk forming a cavity 70. The upper segment 80 of the arms 50 are oriented toward the central axis 30 of the disk 20 and are flexibly attached to elastically bend in a radial direction relative to the center of the disk 20. The bending facilitates attachment of the housing 15 to a medical container, such as a syringe 140, via a snap-fit. A lower segment 90 of the arms 50 extends in a direction away from the central axis 30 such that the arms 20 include flared ends 90 that assist in guiding a mating surface 100 of the medical container into the cavity 70. Inside the cavity 70, on the underside 60 of the disk 20 a series of wells 102, 104 are configured to conform to the dimensions of a transponder 110. A first well 102 generally conforms to the overall dimensions of the transponder 110 and a second well 104, disposed within the first well 102, conforms to the smaller subcomponents 112 of the transponder 110, so that housing of the transponder 110 inside the cavity 70 can be accomplished without damaging it 110. In addition, the underside 60 of the disk 50 may be concave to further enhance protection of the transponder 110 by corresponding to it contours.

The device 10 is shaped and dimensioned to house the transponder 110 inside the cavity 70. In the preferred embodiment, the transponder 110 comprises a passive radio frequency identification (RFID) tag 110 having an integrated circuit, memory, and antenna electrically coupled to the integrated circuit. The RFID tag 110 transmits an electromagnetic signal in response to an electromagnetic signal from an interrogator. The passive RFID tag 110 generates power for the integrated circuit from the incoming electromagnetic signal from the interrogator. In the illustrated embodiment, the RFID tag 110 includes a disk shaped substrate 115 on which the other RFID components are fixed. The RFID tag 110 comprises a secure memory device that is sealed and may include a data storage from 1 kilobit to 64 kilobits and an operating distance up to 10 cm. Additionally, the RFID tag 110 may be capable of 100,000 write cycles and may include a 10 year data retention time period. The RFID tag 110 may have operating temperatures from −40 to +85 degrees C. When attached to a medical container, the radio frequency verification device 10 of the present invention allows communication with one or more data sources and permits verification of medical information and the location of the medical container. By way of example, the medical information may include: patient identification, physician identification, drug identification, method of administration, route of administration, frequency, procedure identification, equipment needed, instruments needed, dates, and other pertinent information.

Figure 4A:
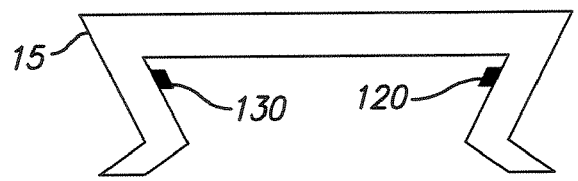
FIG. 4a is a sectional view of a preferred verification system and device depicting a ridge within the housing.
Figure 4B:
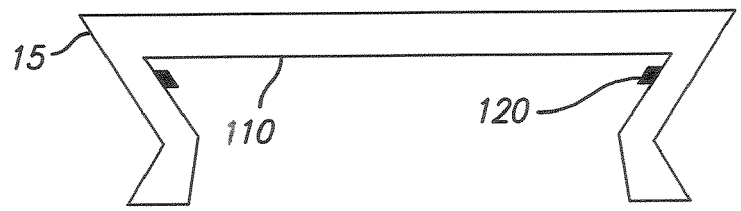
FIG. 4b is a sectional view of a preferred verification system and device depicting a transponder within the housing.
Figure 6:
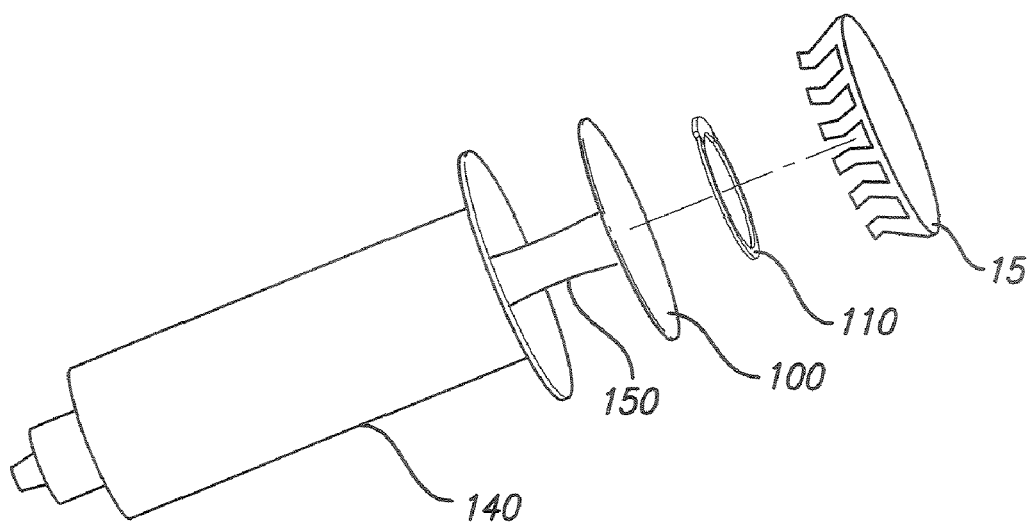
FIG. 6 is a perspective view of a preferred verification system and device and a syringe.

Referring to FIGS. 4a and 4b, located between the arms 50 and the disk 20 is a ring 120 that is integral with the arms 50 and disk 20. Inside the cavity 70, along the ring 120, is a ridge 130 that serves to immobilize the RFID tag 110 and act as a stop for a mating surface 100, thereby preventing damage to the RFID tag 110. The disk shape of the of the RFID tag 110 in combination with the ridge 130, facilitates secure placement of the RFID tag 110 into the housing 15 without the necessity for glue, adhesives, fasteners or the like. According to a preferred implementation of the invention, the mating surface 100 is generally disk shaped and is integral with a plunger 150 of the syringe 140 (as illustrated in FIG. 6). According to other embodiments, mating surface 100 may be integral with a drug container, solutions bag, I.V. administration set, extension set, catheter, transducer or any other medical container without departing from the scope of the invention. When the housing 15 containing the RFID tag 110 is attached to the mating surface 100 (located on the end of the plunger 150), the RFID tag 110 is sandwiched between the underside 60 of the disk 20 and the mating surface 100 thus preventing damage to the RFID tag 110 during actuation of the plunger 150.

Figure 5A:
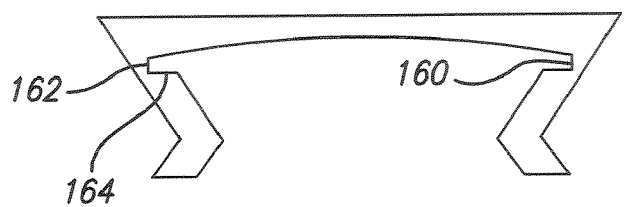
FIG. 5a is a sectional view of a preferred verification system and device depicting a two-sided groove in the housing.
Figure 5B:
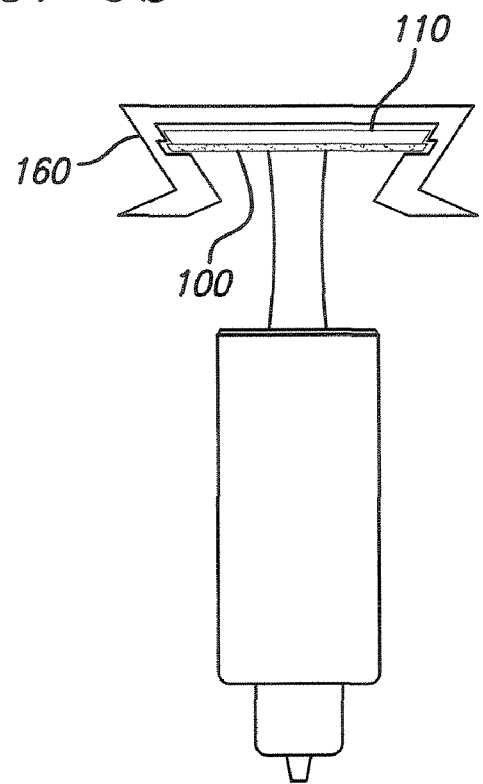
FIG. 5b is a sectional view of a preferred verification system and device depicting a transponder in the housing.
Figure 5C:
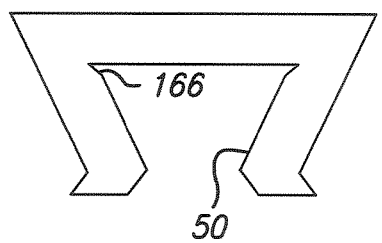
FIG. 5c is a sectional view of a preferred verification system and device depicting a one sided groove in the housing.

Referring to FIGS. 5a, 5b and 5c, the housing 15 may contain a groove 160 disposed within the cavity 70. The groove 160 may comprise a notch within the lower segment 80 of the arms 50 and is comprised of two sides 162, 164. Alternatively, the groove 160 may be formed on the ring 120 inside the cavity 70. In a further alternative embodiment, the groove has one side 166 that is angled with respect to the arms 50. In operation, the groove 160 serves to secure the RFID tag 110 to the mating surface 100 and to prevent damage to the RFID tag 110 during transportation and use. The illustrated groove 160 is merely exemplary and there are numerous ways of machining the housing to contain one or more cutouts and/or projections such as slots, notches, grooves, projections, tabs, steps, stops, angles, that will facilitate attachment of the housing 15 to the mating surface 100 without departing from the scope of the invention. Such cutouts and/or projections may conform or partially conform to one or more surfaces of the RFID tag 110.

Figure 7A:
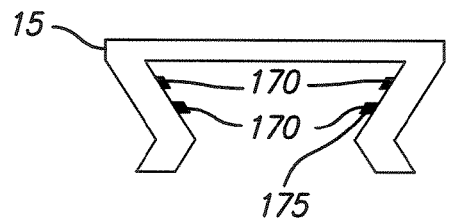
FIG. 7a is a sectional view of a preferred verification system and device depicting a male threads within the housing.
Figure 7B:
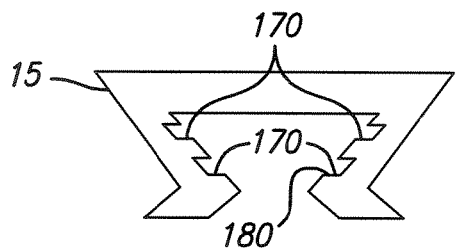
FIG. 7b is a sectional view of a preferred verification system and device depicting female threads within the housing.

Referring to FIGS. 7a and 7b, according to further embodiments of the invention, the housing 15 contains threads 170 on the arms 50 within the cavity 70. In FIG. 7a, the threads 170 are male threads 175, whereas in FIG. 7b, the threads 170 are female threads 180. In either embodiment, the threaded housing 15 is configured to be screwed on to a corresponding threaded mating surface 100 of a medical container. Additionally, the arms 50 of the housing may contain only a single segment and may be disposed substantially normal to the plane of the disk 20.

Figure 8:
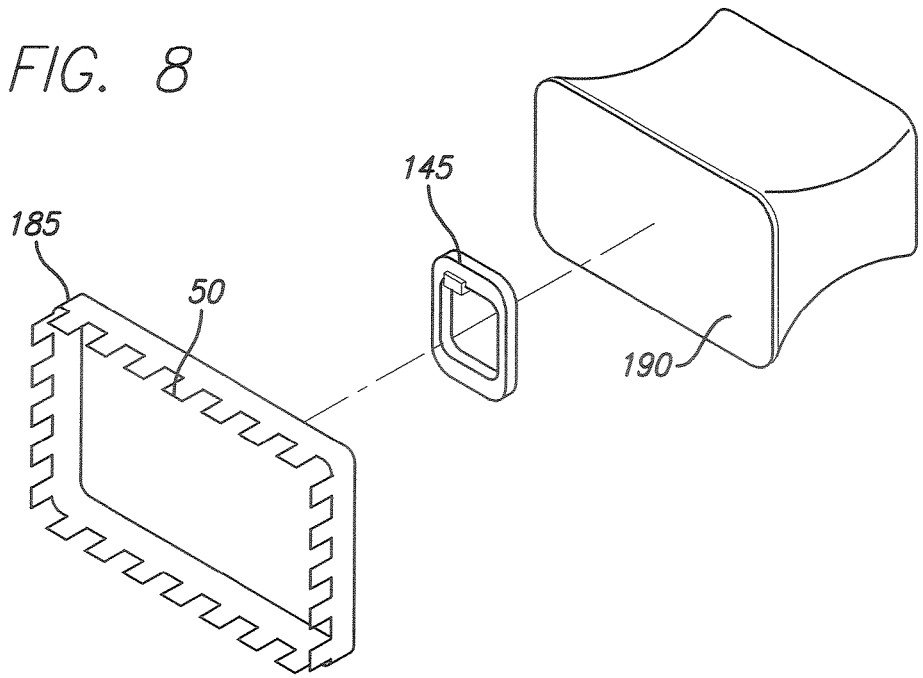
FIG. 8 is a perspective view of an embodiment of the verification system and device depicting a rectangular configuration.

Other embodiments of the invention may include housings that are configured to be attached to variously shaped matting surfaces. By way of example, FIG. 8 illustrates a rectangular shaped housing 185 with arms 50 configured to receive a rectangular matting surface 190 and an RFID tag 195. The invention described herein comprises a removable, snap-on device 10 for containing an RFID tag 110 and for attachment to a medical container such as a syringe 140. Other embodiments may feature an RFID tag 110 that is attached to a wide range of medical containers, such as by taping, gluing, epoxy, ultra violet adhesive, or over-molding. The device allows specific identification, labeling, and other information to be transferred and received via the RF chip, enabling superior safety controls for the administration of any and all drug medications, solutions, and procedures where patient safety is of concern.

In accordance with the principles of the invention, an RFID tag 110 may be attached to a medical device so that the medical device may be tracked as the RFID tag 110 is moved throughout a building such as a hospital. For example, the RFID tag 110 may be tracked using a plurality of stationary RFID interrogators that are placed strategically throughout a hospital. The RFID interrogators are employed to relay the information sent from the RFID tag 110 to a system including a processor such as a PC computer. In operation, an RF interrogator transmits a signal such that when the RFID tag 110 enters an effective range of the RF interrogator, the RF tag 110 transmits a signal containing a unique RF signature to be recorded by the interrogator. According to the invention, the signal may also contain patient and drug identification information. The data received by the interrogator is then uploaded into the system, which can then display and track information regarding a medical container such as a syringe as it moves throughout a medical environment such as a hospital.

Thus, it is seen that a verification system and device is provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

What is claimed is:

1. A radio frequency safety system for a drug container, the system comprising:
    a housing including a cavity; and
    a radio frequency identification tag disposed within the cavity, that stores information and the information may be accessed by a radio frequency signal in response to an incoming radio frequency signal, the transmitted radio frequency signal containing tracking information and drug identification information;
    wherein the housing is attached to the drug container,
    wherein the drug container is a syringe including a plunger having a distal end, and
    wherein the housing is snap-fit onto the distal end of the plunger.

2. The radio frequency safety system of claim 1, further comprising a disk having an outer circumference and a plurality of arms attached to the outer circumference of the disk forming the cavity.

3. A housing for a tracking device, the housing comprising:
    a disk having a central axis and outer circumference; and
    a plurality of arms flexibly attached to the outer circumference of the disk and descending from the disk forming a cavity;
    wherein the tracking device is disposed between the disk and a mating surface of a medical container, and
    wherein the medical container comprises a syringe.

4. The housing of claim 3, wherein the syringe includes a plunger having a distal end, and wherein the housing is snap-fit onto the distal end of the plunger.

5. The housing of claim 3, wherein the tracking device comprises a transponder disposed within the cavity and configured to store information and transmit an electromagnetic signal in response to an electromagnetic wave, the transponder comprising an integrated circuit having a memory and an antenna electrically coupled to the integrated circuit.

* * * * *